US00PP35379P2

(12) United States Plant Patent
Rouwette

(10) Patent No.: US PP35,379 P2
(45) Date of Patent: Sep. 12, 2023

(54) ***HYDRANGEA* PLANT NAMED 'GRHPLF'**

(50) Latin Name: *Hydrangea paniculata*
Varietal Denomination: GRHPLF

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 18/098,095

(22) Filed: Jan. 17, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP16,166 P2 * 12/2005 Van Huylenbroeck ..... Plt./250

* cited by examiner

*Primary Examiner* — June Hwu
(74) *Attorney, Agent, or Firm* — Penny J. Aguirre

(57) ABSTRACT

A new cultivar of *Hydrangea paniculata* plant named 'GRHPLF' that is characterized by its flower panicles that change in color from light green and white to green and becoming increasing blushed with medium pink as they mature, its well-branched plant habit with strong branches, its dwarf to medium plant size, its floriferous blooming habit, and its dense and sturdy flower panicles.

2 Drawing Sheets

Botanical classification: *Hydrangea paniculata.*
Varietal denomination: 'GRHPLF'.

CROSS REFERENCE TO A RELATED APPLICATION

This application is co-pending with a U.S. Plant Patent Application filed for a plant derived from the same breeding program that is entitled *Hydrangea* Plant Named 'GRHP12' (U.S. Plant patent application Ser. No. 18/098,088).

BACKGROUND OF THE INVENTION

The present invention relates to a new and distinct cultivar of *Hydrangea paniculata* and will be referred to hereafter by its cultivar name, 'GRHPLF'. 'GRHPLF' represents a new panicle *Hydrangea*, a perennial shrub grown for landscape use.

The new *Hydrangea* resulted from a controlled breeding program conducted by the Inventor in Valkenburg, The Netherlands. Goals of the breeding program were to develop new cultivars of *Hydrangea paniculata* with sturdy stems, healthy foliage, and unique flower colors. The Inventor made crosses in 2013 between unnamed and unpatented proprietary plants of *Hydrangea paniculata* in the Inventor's breeding program as both the female and male parents. The exact characteristics of the parents are unknown as seeds where pooled and sown from several crosses. 'GRHPLF' was selected as a single unique plant in summer of 2016 from the resulting seedlings of the above crosses.

Asexual propagation of the new cultivar was first accomplished using stem cuttings by the Inventor in summer of 2016 in Valkenburg, The Netherlands. Asexual propagation using stem cuttings has determined that the characteristics of the new cultivar are stable and are reproduced true to type in successive generations

SUMMARY OF THE INVENTION

The following traits have been repeatedly observed and represent the characteristics of the new cultivar. These attributes in combination distinguish 'GRHPLF' as a unique cultivar of *Hydrangea.*

1. 'GRHPLF' exhibits flower panicles that change in color from light green and white to green and becoming increasing blushed with medium pink as they mature.
2. 'GRHPLF' exhibits a well-branched plant habit with strong branches.
3. 'GRHPLF' exhibits a dwarf to medium plant size.
4. 'GRHPLF' exhibits a floriferous blooming habit.
5. 'GRHPLF' exhibits dense and sturdy flower panicles.

'GRHPLF' can be most closely compared to the *Hydrangea paniculata* cultivars 'Limelight' (U.S. Plant Pat. No. 12,874), 'Dvp Pinky' (U.S. Plant Pat. No. 16,166), and 'GRHP12'. 'Limelight' is similar to 'GRHPLF' in having dense flower panicles, a well-branched plant habit, a floriferous blooming habit, and inflorescences with flower panicles that change in color from light green and white to green and pink as they mature. 'Limelight' differs from 'GRHPLF' in having a less dwarfed plant size. 'Dvp Pinky' is similar to 'GRHPLF' in having a well-branched plant habit. 'Dvp Pinky' differs from 'GRHPLF' in having a less dwarfed plant habit and inflorescences with flower panicles that are less dense and more pointed in shape. 'GRHP12' is similar to 'GRHPLF' in having strong branches and dense flower panicles. 'GRHP12' differs from 'GRHPLF' having a smaller plant size, and larger flower panicles that are darker pink in color both early in the season and when mature.

BRIEF DESCRIPTION OF THE DRAWINGS

The accompanying color photographs illustrate the overall appearance and distinct characteristics of the new

*Hydrangea*. The photographs were taken of a three-year-old plant of 'GRHPLF' grown outdoors in a trial field in Boskoop, The Netherlands.

Figure 1:
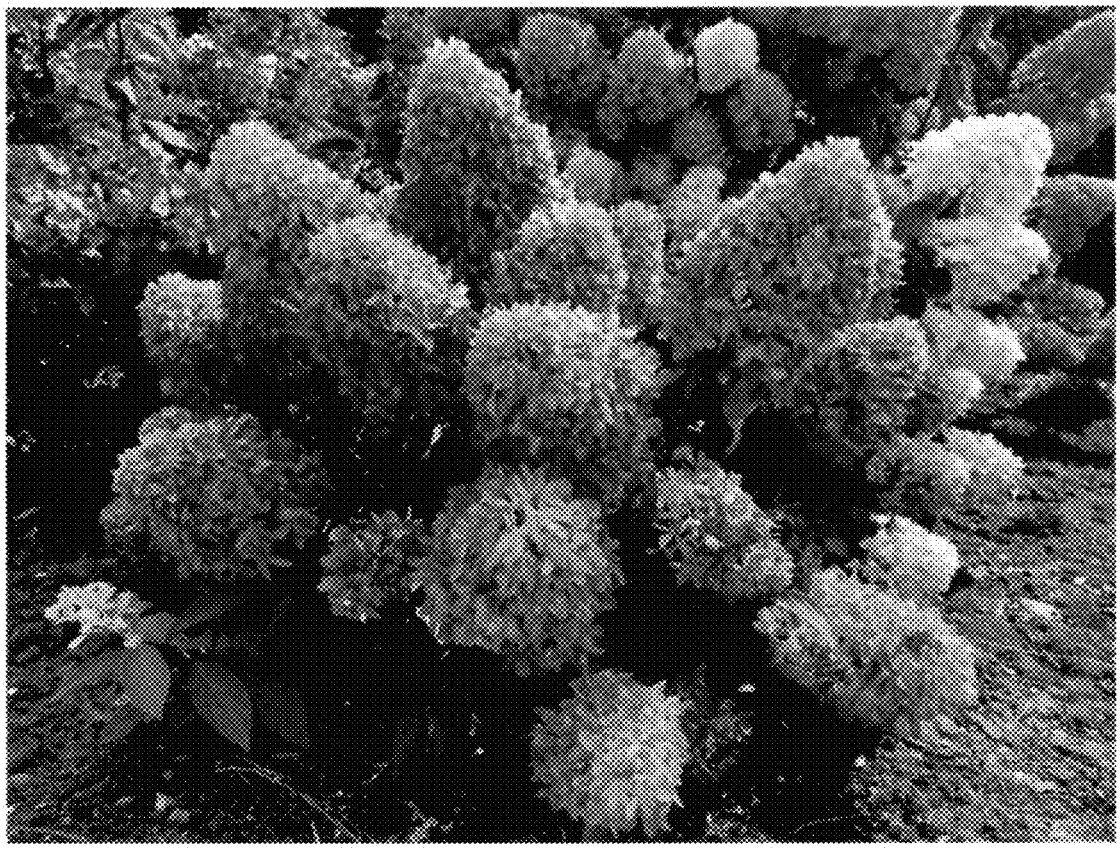

The photograph in FIG. 1 provides a side view of 'GRHPLF' in bloom in fall.

Figure 2:
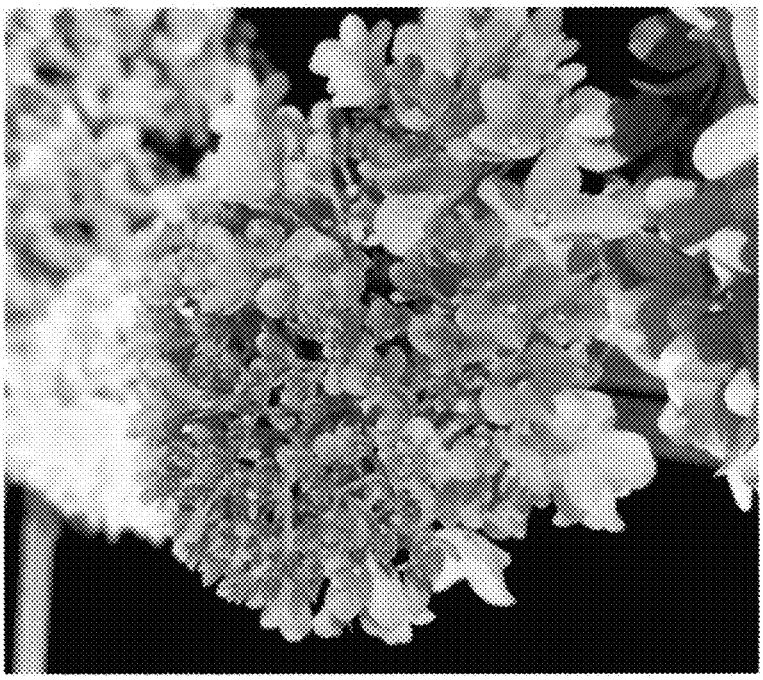

The photograph in FIG. 2 provides a close-up view of an inflorescence of 'GRHPLF' in summer.

Figure 3:
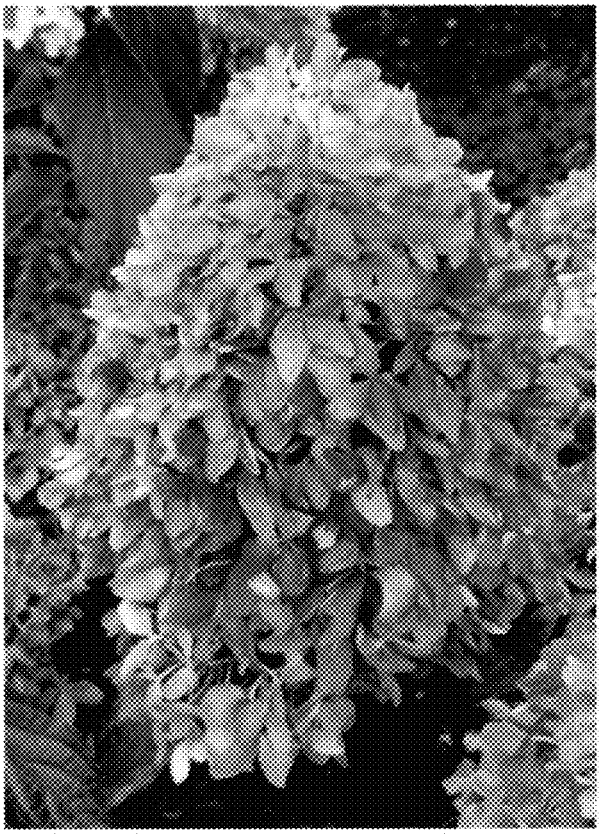

The photograph in FIG. 3 provides a close-up view of an inflorescence of 'GRHPLF' in fall.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of three-year-old plants of 'GRHPLF' as grown outdoors in a trial bed in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-summer through autumn in The Netherlands.

*Plant type*.—Deciduous shrub, panicle type *Hydrangea*.

*Plant habit*.—Medium size, dense, and upright.

*Height and spread*.—Reaches 60 cm in height and 60 to 70 cm in spread in the landscape.

*Hardiness*.—At least in U.S.D.A. Zones 4 to 9.

*Diseases and pests*.—No susceptibility and resistance to diseases or pests has been observed.

*Root description*.—Fibrous, NN155A and 164A in color.

*Propagation*.—Stem cuttings.

*Root development*.—6 to 8 weeks for root initiation with a finished plant produced in in a P9 container in about 12 months from a rooted cutting.

*Growth rate and vigor*.—Moderate.

Stem description:

*Stem shape*.—Rounded.

*Stem strength*.—Strong.

*Stem color*.—Young; 145B, mature; N199B, old bark; 197B.

*Stem size*.—Average of 28 cm in length (excluding inflorescence) and 6 mm in diameter.

*Stem surface*.—Young stems smooth and covered with lenticels an average of 2 mm in length, mature bark is mostly smooth and lacks fasciation.

*Internode length*.—An average of 5 cm.

*Branching*.—Freely branching with an average of 13 lateral branches.

Foliage description:

*Leaf shape*.—Ovate.

*Leaf arrangement*.—Opposite.

*Leaf division*.—Simple.

*Leaf base*.—Obtuse.

*Leaf apex*.—Acute.

*Leaf margins*.—Serrate.

*Leaf venation*.—Pinnate, color; both surfaces 145A.

*Leaf size*.—An average of 9.2 cm in length and 4.8 cm in width.

*Leaf attachment*.—Petiolate.

*Leaf surface*.—Both surfaces; matte, and pubescent.

*Leaf color*.—Young and mature upper surface; 137A, young and mature lower surface 137C.

*Petioles*.—An average of 7 mm in length and 2.5 mm in diameter, both surfaces matte and slightly pubescent, color 145A.

Inflorescence description:

*Inflorescence type*.—Terminal conical panicle, comprised of sterile and fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 18 cm in height and 14 cm in diameter.

*Flower number*.—An average of 200 sterile flowers and 20 fertile flowers per panicle.

*Flower fragrance*.—None.

*Flower size*.—Sterile flowers; up to 3.5 cm in diameter and 1.2 m in depth, fertile flowers; an average of 1 cm in diameter and 4 mm in depth.

*Flower type*.—Sterile flowers rotate, fertile flowers rotate.

*Flower buds*.—Sterile flowers; an average of 6 mm in length and 1.2 cm in diameter, round in shape, NN155D, sometimes a flush of 63B, fertile flowers; an average of 3 mm in length and diameter, ovoid in shape, 145C to 145D in color.

*Petals*.—Sterile flowers; petals do not open and remain in bud stage, fertile flowers; 5, rotate and cruciform in shape, ovate in shape, acute apex, cuneate base, entire margins, average of 3.5 mm in length and 2.5 mm in width, both surfaces matte, color; when opening and fully open upper and lower surface NN155D.

*Peduncles*.—Primary peduncles; strong, flattened oval in shape, an average of 3 cm in length and 2 mm in width. secondary peduncles 2 cm in length and 2 mm in width, 145D in color, surface is matte and pubescent.

*Pedicels*.—Sterile flowers; moderate strength, an average of 1.6 cm in length and 1 mm in width, 145D in color, surface is matte and pubescent, fertile flowers; moderate strength, an average of 2 mm in length, 1 mm in diameter, 145D in color, surface is matte and pubescent.

*Sepals*.—Sterile flowers; 4 to 5, rotate, elliptic to ovate in shape, obtuse apex, acute base, entire margins, average of 1.6 cm in length and 1.4 cm in width, both surfaces; glabrous and matte, color: upper surface when opening; 145A to 145B, lower surface when opening; 145C, when fully open upper surface; 145C, changes to NN155D with flushes of 63B maturing to 63A, fully open lower surface; 63B, flushed with 145A to 145B, changing to 145C with a hint of 63B, fertile flowers; 5, rotate, ovate in shape, acute apex, broad cuneate base, entire margins, 1 mm in length, 1.5 mm in width, both surfaces glabrous and matte, color: when opening and fully open upper and lower surface; NN155D.

Reproductive organs:

*Gynoecium*.—Sterile flowers; flowers do not open, fertile flowers; 1 pistil, an average of 2 mm in length, stigma; club-shaped and 157B in color, style; 1 mm in length, NN155D in color, ovary is 157D in color.

*Androecium*.—Sterile flowers; flowers do not open, fertile flowers; stamens; average of 10, filaments; 3 mm in length, NN155D in color, anthers; broad oblong in shape, 1 mm in length, 155D in color, pollen; low to moderate quantity, 156C in color.

*Fruit and seed*.—None observed to date.

It is claimed:

1. A new and distinct cultivar of *Hydrangea* plant named 'GRHPLF' substantially as herein illustrated and described.

* * * * *